United States Patent
Singleton et al.

(10) Patent No.: US 6,436,372 B2
(45) Date of Patent: Aug. 20, 2002

(54) ORAL COMPOSITION WITH ABRASIVE MIXTURE OF CHALK AND CARBIDE

(75) Inventors: Stephen John Singleton; Matthew Pickles, both of Bebington (GB)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/864,951

(22) Filed: May 24, 2001

(30) Foreign Application Priority Data

May 30, 2000 (EP) .............................. 00304577

(51) Int. Cl.$^7$ ............................................. A61K 7/16
(52) U.S. Cl. ............................................. 424/49
(58) Field of Search ............................ 424/49–88

(56) References Cited

U.S. PATENT DOCUMENTS

| | | | | |
|---|---|---|---|---|
| 3,711,604 A | * | 1/1973 | Colodney et al. | 424/52 |
| 3,929,987 A | * | 12/1975 | Colodney et al. | 424/52 |
| 3,935,306 A | * | 1/1976 | Roberts et al. | 424/49 |
| 3,955,942 A | * | 5/1976 | Cordon et al. | 51/295 |
| 4,089,943 A | * | 5/1978 | Roberts et al. | 424/49 |
| 4,110,083 A | * | 8/1978 | Benedict | 51/295 |
| 4,144,322 A | * | 3/1979 | Cordon et al. | 424/49 |
| 4,157,387 A | * | 6/1979 | Benedict | 424/54 |
| 4,544,377 A | * | 10/1985 | Schwen | 51/298 |
| 4,786,432 A | * | 11/1988 | Kawfer et al. | 252/120 |
| 4,802,950 A | | 2/1989 | Croll | |
| 4,844,883 A | * | 7/1989 | Patel | 424/49 |
| 5,702,811 A | * | 12/1997 | Ho et al. | 428/323 |
| 6,210,625 B1 | * | 4/2001 | Matsushita et al. | 264/610 |

FOREIGN PATENT DOCUMENTS

| | | |
|---|---|---|
| EP | 0 913 144 | 6/1997 |
| WO | 00/10520 | 3/2000 |

OTHER PUBLICATIONS

Abstracts of Wulknitz Advances in Dental Research 11(4): 576–579 Cleaning power and abrasivity of European toothpastes, Nov. 1997.*
Croll Jl. Am. Dent. Assn. 128 Suppl 455–505 Enamel microabrasion, Apr. 1977.*
Hefferren J. Dental. Res. (4): 563–573 A laboratory method for assessment of denti–frice abrasivity, Jul. 1976.*
European Search Report.
Chemical Abstacts, vol. 131, No. 12, Sep. 20, 1999, Abstract No. 158821b.

* cited by examiner

*Primary Examiner*—Shep K. Rose
(74) *Attorney, Agent, or Firm*—Milton L. Honig

(57) ABSTRACT

An oral composition is provided which includes chalk and a particulate material which is selected from silicon carbide or tungsten carbide and has an average particle size ranging from 1 to 10 μm in diameter, the composition delivered in a carrier that includes humectants and optionally other components including anticaries fluoride salts, surfactants and sweetening agents.

6 Claims, No Drawings

ORAL COMPOSITION WITH ABRASIVE MIXTURE OF CHALK AND CARBIDE

BACKGROUND OF THE INVENTION

1. Field of the Invention

The present invention relates to an oral composition with a more effective chalk containing abrasive system.

2. The Related Art

The inclusion of abrasives in oral compositions such as toothpaste is well known. The abrasive has a cleaning as well as a polishing/whitening benefit. The removal of tartar from the tooth surface is thought to reduce the incidence of caries.

Of the abrasives typically used in oral care formulations chalk is one of the most preferred since it is inexpensive and provides an acceptable degree of abrasion for use in oral care.

To improve the abrasivity of a toothpaste composition it is known to use calcined alumina, which is a particulate material having a hardness which is significantly higher than chalk. A disadvantage of calcined alumina is that it is reactive with many of the other ingredients used in toothpastes around the world.

The abrasivity of a toothpaste is measured according to a protocol described in the Journal of Dental Research (1976) 55(4), 563. This describes how the Relative Dental Abrasion (RDA) is evaluated. In Advanced Dental Research Vol 11, (4) pp576–579 is described a method for evaluating the Pellicle Cleaning Ratio (PCR) which is commonly used as a measure of cleaning.

Ideally, a toothpaste will be capable of cleaning the teeth without wearing down the tooth enamel and dentine. So while it is necessary to have a cleaning efficacy a toothpaste with too high an RDA is undesirable.

While the RDA of chalk is generally accepted it would be of great benefit to the consumer if it could be reduced without compromising the cleaning efficacy.

It is also important that the materials used as abrasive do not react with any of the other material commonly used in toothpastes.

SUMMARY OF THE INVENTION

We have surprisingly found that the inclusion of certain hard particulate material in a chalk-containing oral composition can in fact reduce the RDA of the composition while actually maintaining or improving the PCR.

Accordingly, the invention provides an oral composition with an abrasive system of chalk in combination with a particulate material selected from silicon carbide or tungsten carbide, these having an average particle size ranging from 1 to 10 $\mu$m in diameter.

The particulate material of the invention has an average particle size preferably ranging from 0.1 to 10 $\mu$m in diameter, preferably from 1 to 7 $\mu$m and especially from 1.5 to 3 $\mu$m.

The particulate material used in the invention is tungsten carbide, which has an average particles size in the region of 1.6 $\mu$m or silicon carbide, which has an average particles size in the region of 2 $\mu$m.

DETAILED DESCRIPTION

The oral composition according to the invention comprises further ingredients which are common in the art, such as:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates;

vitamins such as Vitamins A, C and E;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.;

flavours, e.g. peppermint and spearmint oils;

other proteinaceous materials such as collagen;

preservatives;

opacifying agents;

colouring agents;

pH-adjusting agents;

sweetening agents;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition.

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

The oral compositions may be in any form common in the art, e.g. toothpaste, gel, mousse, aerosol, gum, lozenge, powder, cream, etc. and may also be formulated into systems for use in dual-compartment type dispensers.

Embodiments according to the present invention will be further illustrated by way of the following example.

EXAMPLE

The following experiment illustrates how the use of a particulate material according to the invention may reduce the RDA of a standard chalk toothpaste while improving the PCR.

The RDA and PCR were measured using the protocols referred to above.

The paste used was a standard paste commonly used in the art. Precipitated calcium carbonate (PCC) was the chalk abrasive used to illustrate the effect of the tungsten carbide (WC).

| Abrasives used | RDA | PCR |
| --- | --- | --- |
| PCC | 125.61 | 80.52 |
| PCC + 0.25% w/w WC | 103.83 | 84.62 |
| PCC + 0.5% w/w WC | 87.65 | 91.95 |

What is claimed is:

1. Oral composition comprising:
   (a) from 3 to 60% by weight of a composition of particulate abrasive materials comprising:
      (i) chalk; and
      (ii) a particulate material selected from the group consisting of silicon carbide and tungsten carbide and having an average particle size ranging from 1 to 10 $\mu$m in diameter, the chalk and particulate material being present in an effective amount to reduce the RDA while maintaining or improving the PCR of the composition relative to a chalk-containing oral composition without the particulate material; and
   (b) a humectant present in an effective amount to serve as a carrier for the abrasives.

2. Oral composition according to claim 1, wherein the particulate material has an average particle size ranging from 1 to 7 $\mu$m in diameter.

3. Oral composition according to claim 2, further comprising a fluoride salt in an effective amount to prevent formation of caries.

4. Oral composition according to claim 2, further comprising a surfactant present in an effective amount to generate foam.

5. Oral composition according to claim 2, further comprising a sweetening agent in an effective amount to sweeten the oral composition.

6. Oral composition comprising:
   (a) an abrasive system comprising:
      (i) chalk; and
      (ii) a particulate material selected from the group consisting of silicon carbide and tungsten carbide and having an average particle size ranging from 1 to 10 $\mu$m in diameter, the chalk and particulate material being present in an effective amount to reduce RDA while maintaining or improving PCR of the composition relative to a chalk containing oral composition without the particulate material; and
   (b) a surfactant present in an effective amount to generate foam in an oral cavity.

* * * * *